US010702911B2

(12) United States Patent
Tochimura et al.

(10) Patent No.: US 10,702,911 B2
(45) Date of Patent: Jul. 7, 2020

(54) MEDICAL SUTURE NEEDLE (71) Applicants: Yoshimasa Tochimura, Utsunomiya (JP); Satoshi Tetsuka, Utsunomiya (JP); Kazuaki Kato, Utsunomiya (JP)

(72) Inventors: Yoshimasa Tochimura, Utsunomiya (JP); Satoshi Tetsuka, Utsunomiya (JP); Kazuaki Kato, Utsunomiya (JP)

(73) Assignee: MANI, Inc., Utsunomiya (JP)

(*) Notice: Subject to any disclaimer, the term of this patent is extended or adjusted under 35 U.S.C. 154(b) by 503 days.

(21) Appl. No.: 15/608,929

(22) Filed: May 30, 2017

(65) Prior Publication Data
US 2018/0043419 A1 Feb. 15, 2018

Related U.S. Application Data (62) Division of application No. 12/990,019, filed as application No. PCT/JP2009/057998 on Apr. 22, 2009, now abandoned.

(51) Int. Cl.
B21G 1/08 (2006.01)
A61B 17/06 (2006.01)
(Continued)

(52) U.S. Cl.
CPC .......... B21G 1/08 (2013.01); A61B 17/06066 (2013.01); B21G 1/003 (2013.01);
(Continued)

(58) Field of Classification Search
CPC . B21G 1/00; B21G 1/003; B21G 1/12; B21G 1/08; A61B 17/06066; A61B 2017/0608; D05B 85/06; B24B 19/16
See application file for complete search history.

(56) References Cited

U.S. PATENT DOCUMENTS 3,160,157 A * 12/1964 Chisman .......... A61B 17/06066
606/223
4,799,483 A * 1/1989 Kraff ................ A61B 17/06066
606/226
(Continued)

FOREIGN PATENT DOCUMENTS

EP 0107961 5/1984
EP 0582276 2/1994
(Continued)

OTHER PUBLICATIONS

Translation; JP 1-195892A; Aug. 1989.*
International Search Report issued in counterpart International Application No. PCT/JP2009/057998.

Primary Examiner — Edward T Tolan
(74) Attorney, Agent, or Firm — Shlesinger, Arkwright & Garvey LLP (57) ABSTRACT The goal is to provide a medical suture needle having, as the material, austenite stainless steel with a structure that is elongated in a fiber form while improving the hardness and flexural strength of the cutting portion. A medical suture needle is made of austenite stainless steel having a structure that is elongated in fiber form, and has a cutting portion and a body portion with a triangular cross-sectional shape that is continuous with said cutting portion. The cutting portion has cutting edges, at least one surface of which is formed by a pressed surface, and which are formed by the intersection of said pressed surface with two sharpened surfaces, and a cutting edge that is formed by the intersection of the two sharpened surfaces. The tip where the various cutting edges and converge is positioned in the center of the pressed surface. Moreover, the cutting edges formed by the intersection of the above pressed surface with the two sharpened surfaces are longer than the cutting edge that is formed by the intersection of the two sharpened surfaces.

5 Claims, 7 Drawing Sheets (51) Int. Cl.
*B24B 19/16* (2006.01)
*B21G 1/00* (2006.01)

(52) U.S. Cl.
CPC ...... *B24B 19/16* (2013.01); *A61B 2017/0608* (2013.01); *A61B 2017/06071* (2013.01)

(56) References Cited

U.S. PATENT DOCUMENTS

| | | | | |
|---|---|---|---|---|
| 5,155,943 A | * | 10/1992 | Matsutani | A61B 17/06066 163/5 |
| 5,178,628 A | * | 1/1993 | Otsuka | A61B 17/06066 163/5 |
| 5,330,441 A | * | 7/1994 | Prasad | A61B 17/06066 606/222 |
| 5,411,613 A | * | 5/1995 | Rizk | A61B 17/06066 148/606 |
| 5,476,480 A | * | 12/1995 | Matsutani | A61B 17/06066 606/222 |
| 5,571,042 A | * | 11/1996 | Abbate | A61B 17/06066 451/57 |
| 5,749,897 A | | 5/1998 | Matsutani | |
| 5,897,572 A | | 4/1999 | Schulsinger et al. | 606/224 |
| 5,928,268 A | * | 7/1999 | Butwell | B21G 1/08 163/5 |
| 6,322,581 B1 | * | 11/2001 | Fukuda | A61B 17/06066 606/222 |
| 7,353,683 B2 | * | 4/2008 | Bogart | B21G 1/00 163/5 |
| 8,062,332 B2 | * | 11/2011 | Cunningham | A61B 17/06066 606/222 |

FOREIGN PATENT DOCUMENTS

| | | | |
|---|---|---|---|
| EP | 0698375 | 2/1996 | |
| JP | 1-195892 A | * 8/1989 | ....... A61B 17/06066 |
| JP | H05-56983 A | 3/1993 | |
| JP | 8-57566 A | 3/1996 | |
| JP | 2001-333909 A | 12/2001 | |
| JP | 2001-333910 A | 12/2001 | |

\* cited by examiner

MEDICAL SUTURE NEEDLE

Cross-Reference to Related Applications

This application is a Divisional application of application Ser. No. 12/990,019, filed Jan. 7, 2011, which is a 371 National Stage application of application No. PCT/JP2009/057998, filed Apr. 22, 2009, and which claims the priority of Japanese application No. JP 2008-118171, filed Apr. 30, 2008, and each of which is incorporated herein by reference.

TECHNICAL FIELD

The present invention relates to a medical suture needle used for suturing a cut affected area, and particularly to a medical suture needle whose tip has enhanced hardness.

BACKGROUND ART

A medical suture needle (hereinafter referred to as a suture needle) has a sharp tip at its leading end portion. There are a needle having plural cutting edges arranged from this sharp tip, and a needle having a cross-section formed into generally a circle from the sharp tip without having a cutting edge. Various standards are set for a shape or thickness I and various types of suture needles are provided for every standard. A doctor appropriately selects one of these suture needles according to the various conditions such as a living tissue or a region that should be sutured.

A needle having cutting edges is formed to have a cutting portion formed at its leading end portion, a body portion formed continuous with the cutting portion, and a proximal end part that is formed continuous with the body portion and is provided with a hole for connecting a suture thread. The body portion is a portion that should be gripped by a needle holder during an operation, and the cross-section thereof is formed into a polygon including a triangle. The proximal end part includes the one having a cross-section that is formed into an ellipse corresponding to the shape of the hole for connecting the suture thread, and the one having the cross-section formed into a circle.

The suture needle in which the cross-section of the body portion has a polygonal shape including a triangular shape as described above is generally formed by press-molding the body portion. The suture needle in which the cross-section of the cutting portion is polygonal including a triangle shape is formed as described below. Specifically, the portion corresponding to the cutting portion is roughly formed by a press working, and then, the respective surfaces are ground to form cutting edges at the intersection part of the respective surfaces. Alternatively, plural surfaces are formed by grinding without performing a rough forming through the press working, and cutting edges are formed at the intersection part of the respective surfaces.

Figure 6:
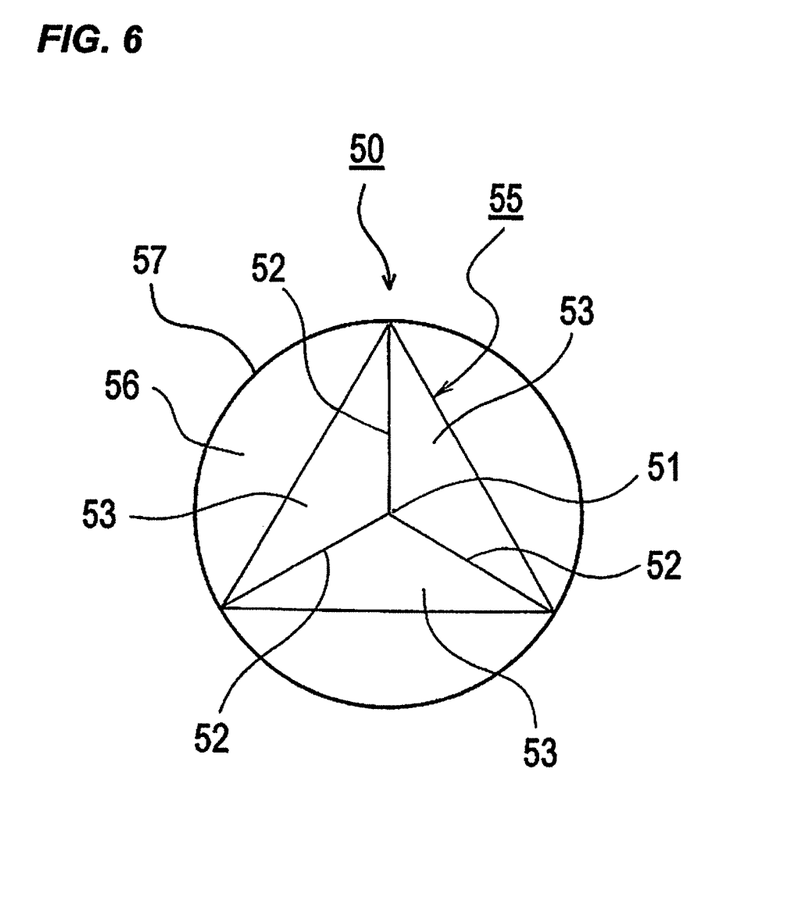
FIG. 6 is a view illustrating a structure of a part of a conventional suture needle (R needle).

A representative example of the suture needle described above will be described with reference to FIGS. 6 and 7. A suture needle 50 illustrated in FIG. 6 is a so-called R needle. It is made as a curved needle (see FIG. 1) that is curved with a curvature set beforehand. A sharp tip 51 is formed at its leading end, and three cutting edges 52 are formed from the sharp tip 51. The respective cutting edges 52 are formed by the intersection of two grinded surfaces 53. The portion including the sharp tip 51 and the cutting edges 52 is formed into a cutting portion 55, and the portion continuous with the cutting portion 55 is formed as a body portion 56 having a triangular cross-section. A proximal end part 57 that couples a suture thread is formed continuous with the body portion. In the suture needle 50, the sharp tip 51 is formed so as to agree with the center of the thickness.

In the suture needle 50 described above, all of three surfaces of the cutting portion 55 are the grinded surfaces 53. However, there has been known a suture needle in which two surfaces are defined as pressed surfaces formed by a press-molding, and one surface is formed as a grinded surface, wherein a cutting edge is formed at the intersection of the pressed surface and the grinded surface. When one surface is formed as the grinded surface as described above, the surface is heavily ground after the press to sharpen the cutting edge, in order to afford sharpness.

Figure 7:
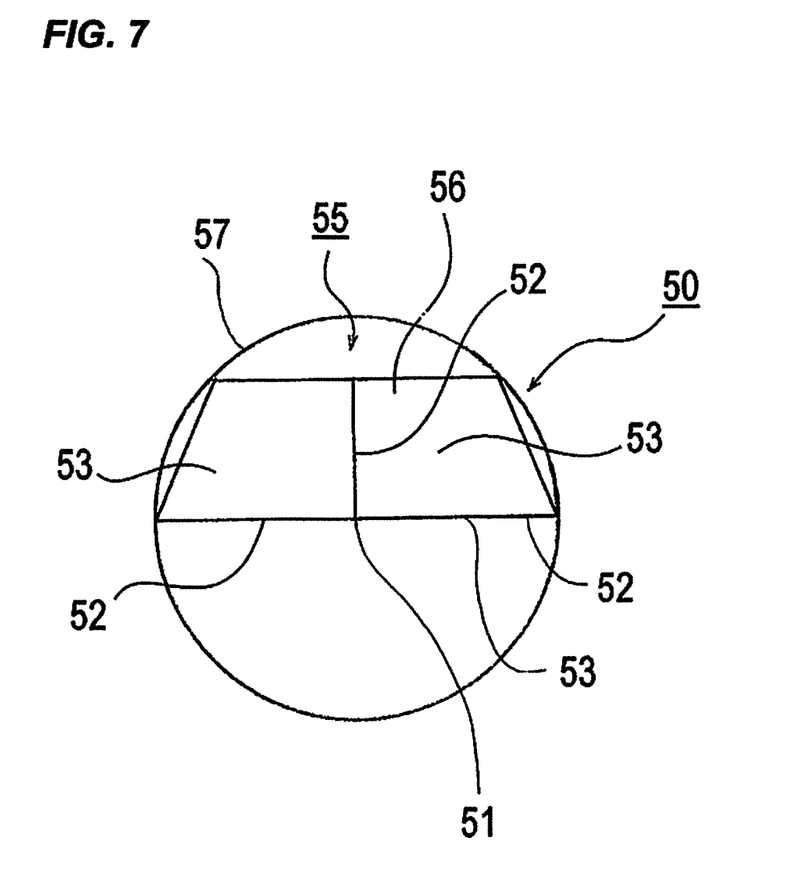
FIG. 7 is a view illustrating a structure of a part of a conventional suture needle (P needle).

A suture needle illustrated in FIG. 7 is a so-called P needle. Like the R needle, a sharp tip 51 is formed at the leading end, wherein three cutting edges 52 are formed from the sharp tip 51, and the respective cutting edges 52 are formed by the intersection of two grinded surfaces 53. The portion including the sharp tip 51 and the cutting edge 52 is formed as a cutting portion 55, and the portion continuous with the cutting portion 55 is formed as a body portion 56 having an elliptic cross-section formed by a press-forming. A proximal end part 57 that couples a suture thread is also formed continuous with the body portion 56. In the suture needle SO, the sharp tip 51 is formed so as to agree with the center of the thickness.

The invention described in Patent Document 1 relates to a suture needle that passes through a calcified living tissue or bone for use. This suture needle has plural flat surfaces for forming one or more cutting edges at the cut part. The cutting edge is converged toward the sharp tip, and two or more another crossing flat surfaces for forming additional cutting edges are formed at the sharp tip. This suture needle can relatively easily pass through a hard living tissue.

On the other hand, there has been proposed, as a material of the suture needle, the one in which an austenitic stainless steel is subject to a cold wiredrawing process with a predetermined reduction of area, whereby a work hardening is generated to enhance hardness, and an austenitic structure is elongated in a fiber to enhance bending strength. When the suture needle is produced with the use of this material, a generation of rust can be prevented during a distribution, thus advantageous.

[Patent Document 1]
 Japanese Patent Application Publication No. 3-70493

DISCLOSURE OF THE INVENTION

Problems to be Solved by the Invention

In the suture needle described in the Patent Document 1, which passes through a calcified living tissue or bone to suture an affected region, the sharp tip and the cutting edge from the sharp tip has to be sufficiently hard. However, in the austenitic stainless steel having a structure elongated in a fiber, a hardness distribution in the cross-section is such that the hardness at the center and on the surface is low, and the portion slightly inward from the surface toward the center has the highest hardness, although the work hardening is produced by the cold wiredrawing process.

Therefore, when the cutting portion including the sharp tip and the cutting edge from the sharp tip is formed by a grinding, the portion having the highest hardness might be removed by the grinding, which entails a problem that a sufficient hardness cannot be attained. This can be applied to the case in which the portion corresponding to the cutting portion is roughly formed by a press working, and then, formed by a grinding, and the case in which the cutting portion is formed only by the grinding without performing the roughly forming with the press working, regardless of the shape of the cross-section of the body portion.

The conventional example in which the cross-section of the body portion has a triangular shape, and two surfaces are formed as the pressed surfaces, and one surface is formed as a grinded surface, tends to have a weak bending strength at the cutting portion, since the ground amount is large in order to afford sharpness. Under the current situation, the grinding time cannot be shortened as is expected, because an operation of forming a grinding stone surface into a shape of the grinded surface of the suture needle is needed.

As described above, the suture needle produced with the use of the austenitic stainless steel having a structure that is elongated in a fiber as a material has a problem that there is a limitation in the hardness and bending strength of the cutting portion including the sharp tip and the cutting edge formed from the sharp tip.

The present invention aims to provide a suture needle that is made of an austenitic stainless steel having a structure that is elongated in a fiber and that has a cutting portion with enhanced hardness and bending strength.

Means to Solve the Problems

In order to solve the above-mentioned problem, the medical suture needle according to the present invention is made of an austenitic stainless steel having a structure that is elongated in a fiber, the needle including a cutting portion, and a body portion that is continuous with the cutting portion and that has a triangular cross-section, wherein the cutting portion has one surface made of a pressed surface, a cutting edge formed by the intersection of ~he pressed surface and two grinded surfaces, and a cutting edge that is formed by the intersection of two grinded surfaces, wherein a leading end where the respective cutting edges are concentrated is positioned at the center of the pressed surface.

In the medical suture needle, it is preferable that the cutting edges formed by the intersection of the pressed surface and two grinded surfaces are longer than the cutting edge formed by the intersection of two grinded surfaces.

In the medical suture needle, it is preferable that a crest is formed on the surface opposite to the pressed surface, and the grinded surface is formed by grinding the surface having the crest formed thereon.

In the medical suture needle, it is preferable that one end of the cutting edge formed by the intersection of two grinded surfaces is connected to a sharp tip of the medical suture needle, while the other end is continuous with an extension line of the crest at the cutting portion.

Another medical suture needle according to the present invention is made of an austenitic stainless steel having a structure that is elongated in a fiber, the needle including a cutting portion; and a body' portion that is continuous with the cutting portion and that has an elliptic shape, wherein the cutting portion has upper and lower surfaces made of pressed surfaces, cutting edges formed by the intersection of one of the upper and lower pressed surfaces and two grinded surfaces, and a cutting edge that is formed by the intersection of two grinded surfaces, wherein a leading end where the respective cutting edges are concentrated is positioned at the center of the pressed surface that intersects the two grinded surfaces to form the cutting edges.

In the medical suture needle described above, it is preferable that one of the upper and lower pressed surfaces is ground to form two grinded surfaces, and that the intersection of the other pressed surface and the two grinded surfaces and the intersection of the two grinded surfaces are formed as cutting edges.

In the medical suture needle described above, it is preferable that the cutting edges formed by the intersection of the pressed surface and two grinded surfaces are longer than the cutting edge formed by the intersection of the two grinded surfaces.

In the medical suture needle described above, it is preferable that one end of the cutting edge formed by the intersection of two grinded surfaces is connected to a sharp tip of the medical suture needle, while the other end is continuous with the pressed surface, of one of the upper and lower pressed surfaces, which does not form the cutting edge.

Effects of the Invention

In the medical suture needle described above, the cutting portion has at least one surface that is the pressed surface. Specifically, the pressed surface is formed by the surface of the austenitic stainless steel having a structure that is elongated in a fiber. Therefore, the portion that is slightly inward from the surface toward the center and that has the highest hardness is left, although the hardness of the surface is lowered. Accordingly, in the cutting edge formed by the intersection of the pressed surface and the two grinded surfaces, the portion crossing the pressed surface and having the highest hardness is exposed, although the hardness of the cutting edge is lowered toward the center. Therefore, the hardness of the sharp tip and the cutting edge from the sharp tip can be enhanced.

Since the cutting portion is subject to a press working, a work hardening is produced. Further, the two surfaces are formed as the grinded surfaces. Therefore, compared to the conventional example, a sharp cutting edge having high hardness with a less grinding amount can be formed.

Since the cutting edges formed by the intersection of the pressed surface and the two grinded surfaces are longer than the cutting edge formed by the intersection of the two grinded surfaces, the cross-sectional area of the cutting portion can be increased compared to the conventional example, and further, the cutting edge having high hardness sufficiently extends from the leading end to the body portion. Therefore, a cross-sectional secondary moment is great, so that the bending strength is great. Moreover, the cutting portion can be formed as the part having the cutting edge with high hardness. Consequently, the present invention can provide a medical suture needle that can easily pass through even a hard living tissue.

BEST MODE FOR CARRYING OUT THE INVENTION

Most preferable embodiments of the medial suture needle according to the present invention will be described below. The medical suture needle according to the present invention includes a very hard sharp tip and a cutting edge that is formed from the sharp tip, although made of an austenitic stainless steel having a structure that is elongated in a fiber. Therefore, a piercing ability can be enhanced.

In the medical suture needle according to the present invention, the portion corresponding to the cutting portion made of the austenitic stainless steel having a structure that is elongated in a fiber is subject to a press working to be formed as a pressed surface, wherein two surfaces that are at the back of the pressed surface are ground to be formed as grinded surfaces, and the intersections of the pressed surface and the grinded surfaces are formed as the cutting edges.

Since the material is subject to the press working as described above, the material, which is subject to a cold wiredrawing process beforehand to have a structure elongated in a fiber, and which has a work hardening because of the cold wiredrawing process, can further be hardened. Moreover, at least one surface constituting the cutting portion is formed as the pressed surface, whereby the portion, having the high hardness, in the cross-section of the material made of the austenitic stainless steel having a structure that is elongated in a fiber can be utilized as it is without performing the grinding process.

Therefore, the cutting edges formed by the intersection of the pressed surface and the grinded surfaces are composed of the portion hardened by the press working and the port ion hardened by the cold wiredrawing process, with the result that the cutting edges can exhibit high hardness.

The medical suture needle according to the present invention Also has the cutting edge formed by the intersection of two grinded surfaces. This cutting edge and two cutting edges formed by the intersection of the pressed surface and the two grinded surfaces are concentrated on the leading end portion. In the cutting edge formed by the intersection of the two grinded surfaces, the portion having high hardness in the material is removed by the grinding process, so that the cutting edge has lower hardness compared to the hardness of the cutting edges formed by the intersection of the pressed surface and the grinded surfaces. However, at the leading end portion where three cutting edges are concentrated, the portion having high hardness of the material remains, whereby high hardness can be exhibited. Accordingly, the medical suture needle according to the present invention can exhibit satisfactory piercing ability.

In the medical suture needle according to the present invention, among the three cutting edges, the cutting edges formed by the intersection of the pressed surface and the grinded surfaces are longer than the cutting edge formed by the intersection of two grinded surfaces. Therefore, two cutting edges having high hardness are present at the cutting portion constituting the suture needle with a sufficient length. Accordingly, the resistance upon passing through a living tissue can be reduced. Since the cross-sectional area of the cutting portion is greater than that in the conventional example, the cross-sectional secondary moment is increased, and hence, the bending strength can be increased. This structure is particularly effective, when applied to a suture needle including a body portion having a triangular cross-section.

In the present invention, the shape of the suture needle is not particularly limited. A curved needle that is curved with a predetermined radius of curvature and angle or a straight needle may be employed. The usage is not particularly limited. The suture needle according to the present invention can be applied to be used for a living tissue such as a skin or muscle or a relatively hard living tissue such as a bone. However, since the hardness at the cutting port ion is enhanced, the medical suture needle according to the present invention is particularly effective when applied to be used for a relatively hard living tissue, e.g., a calcified living tissue or bone.

The portion that is to become the cutting portion with two grinded surfaces being formed may be press-formed in such a manner that two surfaces forming two grinded surfaces tilt from the body portion toward the leading end portion where the respective cutting edges are concentrated. With this structure, not only two cutting edges formed by the intersection of the pressed surface and the two grinded surfaces I but also the cutting edge formed by the intersection of the two grinded surfaces can exhibit high hardness.

DETAILED DESCRIPTION OF THE INVENTION

Embodiment 1

Figure 1A:
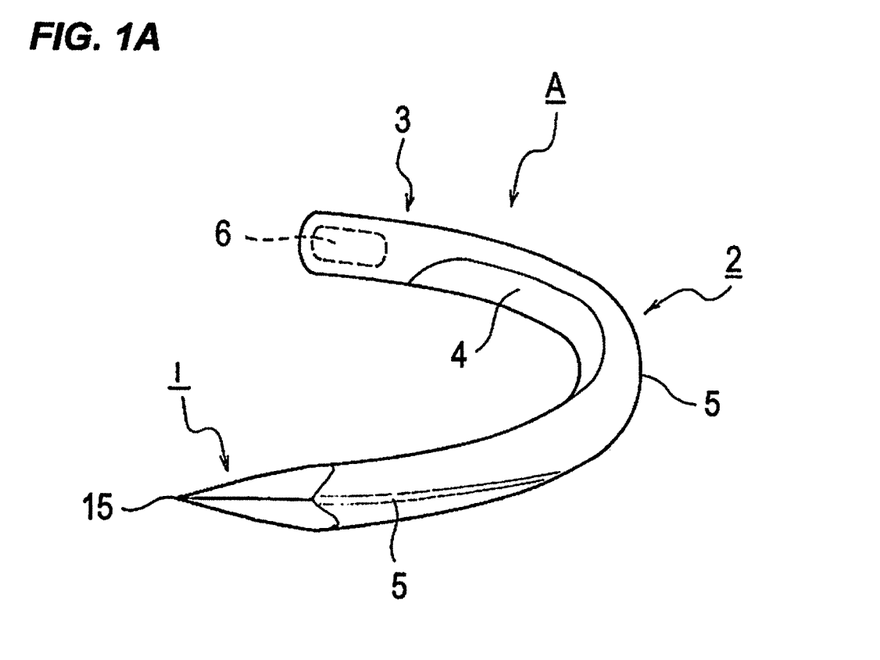
FIG. 1A is a view illustrating an overall structure of a suture needle according to an embodiment of the present invention.
Figure 1B:
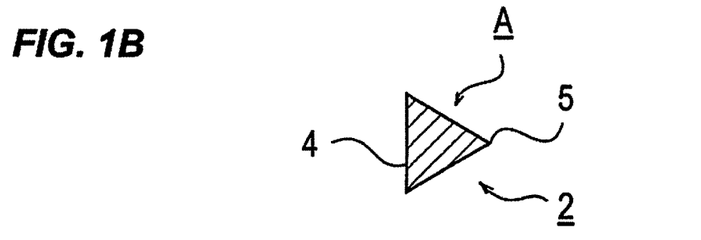
FIG. 1B is a further view illustrating an overall structure of a suture needle according to an embodiment of the present invention.
Figure 2A:
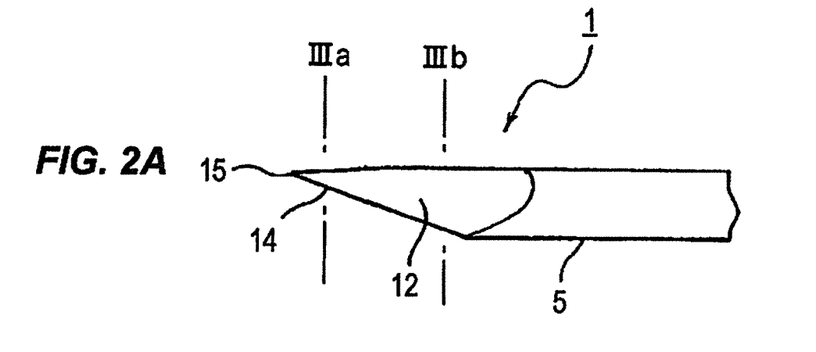
FIG. 2A is a view illustrating a structure of a leading end portion of the suture needle including a cutting portion.
Figure 2B:
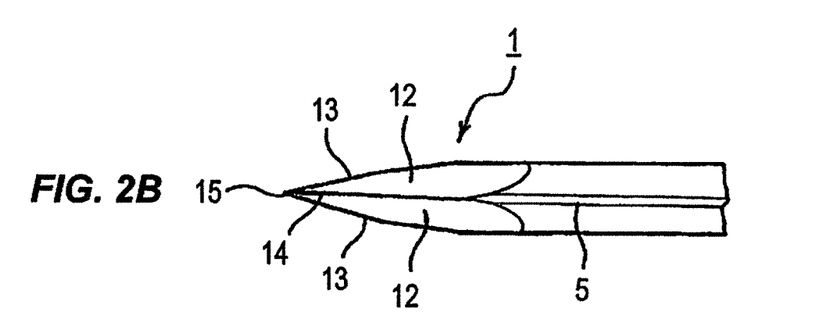
FIG. 2B is a further view illustrating a structure of a leading end portion of the suture needle including a cutting portion.
Figure 2C:
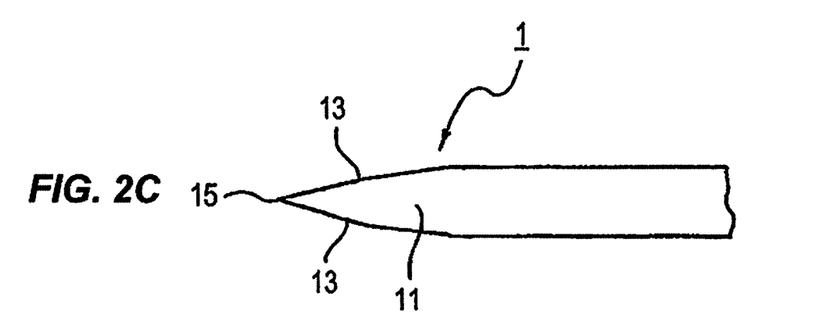
FIG. 2C is a further view illustrating a structure of a leading end portion of the suture needle including a cutting portion.
Figure 3A:
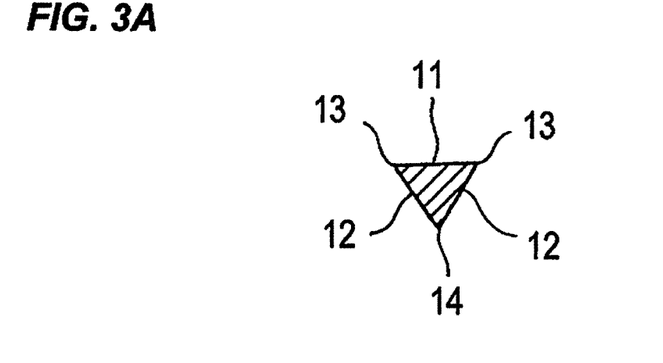
FIG. 3A is a sectional view, corresponding to FIGS. 2A and 2B, illustrating the cross-sectional shape of the leading end portion of the suture needle.
Figure 3B:
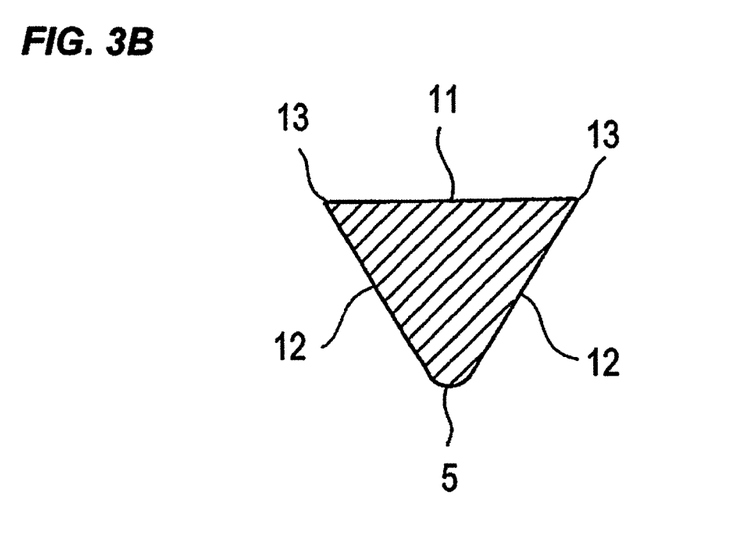
FIG. 3B is a further sectional view, corresponding to FIGS. 2A and 2B, illustrating the cross-sectional shape of the leading end portion of the suture needle.

A structure of a medical suture needle according to a first embodiment will next be described with reference to the drawings. FIG. 1 is a view illustrating an overall structure of the medical suture needle according to the present embodiment. FIG. 2 is a view illustrating a structure of a leading end portion of the suture needle including a cutting portion. FIG. 3 is a sectional view, corresponding to FIGS. 2(*a*) and 2(*b*), illustrating the cross-sectional shape of the leading end portion of the suture needle.

Firstly, the overall structure of the medical suture needle A will be described with reference to FIG. 1. The suture needle A is formed as a curved needle that is curved with a predetermined radius of curvature and a curved angle. As described above, the medical suture needle according to the present invention is not limited to the curved needle in the present embodiment, but may be a straight needle formed into a straight shape. The present embodiment does not limit the overall shape.

The suture needle A has a cutting portion 1 at the leading end. A body portion 2 is formed continuous with the cutting portion 1. In the suture needle A in the present embodiment, the body portion 2 has a plane 4 on the curved inner surface, and has a crest 5 on the curved outer surface, by a press working. Specifically, the cross-section of the body portion 2 is formed into a triangle (see FIG. 1 (b)). The respective apexes of the triangle are formed by a curved line in order to prevent the body portion 2 from giving damage to a living tissue when it passes through the living tissue. The body portion 2 is also formed so as to be capable of stably being held by a needle holder with the plane 4 and the crest 5.

A proximal end part 3 having substantially a circular cross-section is formed continuous with the body portion 2. A blind hole 6 having a predetermined depth is formed on the end surface of the proximal end part 3. When a suture thread is inserted into the blind hole 6, and the proximal end part 3 is caulked, the inserted suture thread can be connected to the suture needle A. The hole for connecting the suture thread is not limited to the blind hole 6 in the present embodiment. It may be configured such that the proximal end part 3 is formed Into an elliptic shape to form a pair of columns having spring performance, wherein a suture thread passes through a space formed between the spring columns so as to be connected to the suture needle.

The cutting portion 1 has one pressed surface 11 and two grinded surfaces 12. The cutting portion 1 is composed of two cutting edges 13 formed by the intersection of the pressed surface 11 and the respective grinded surfaces 12, and one cutting edge 14 formed by the intersection of two grinded surfaces 12. The respective cutting edges 13 and 14 are concentrated toward the leading end, and the point where they are concentrated is formed as a sharp tip 15.

The pressed surface 11 is formed such that an austenitic stainless steel, in which a structure is elongated in a fiber by performing a cold wiredrawing process beforehand to a material of the suture needle A, is cut corresponding to the length of the target suture needle A to forma material, and its end portion is subject to a press working.

Specifically, one end portion of the material is subject to the press working, whereby the pressed surface 11 constituting the cutting portion 1 is formed. The plane 4 and the crest 5 are formed on the portion of the material Corresponding to the body portion 2 with the press working. Accordingly, the pressed surface 11 is continuous with the body portion 2 at its one end.

The crest 5 is formed at the side opposite to the pressed surface 11 formed on the portion corresponding to the cutting portion 1, and formed so as to reach the out ting port ion 1. The cutting portion 1, which has not conventionally been subject to the press working, is subject to the press working to form the pressed surface 11, whereby the hardness of the portion where the pressed surface 11 is formed can be increased.

The grinded surfaces 12 are formed by grinding the surfaces opposite to the pressed surface 11, i.e., the surfaces on which the crest 5 is formed. The angle of the grinded surface 12 to the pressed surface 11 is equal to the angle to the portion where the pressed surface 11 is formed. Therefore, the cutting edges 13 are formed from the sharp tip 15 of the pressed surface 11 to the connection portion of the body portion 2.

The grinded surfaces 12 cross each other at the portion close to the sharp tip 15, whereby forming the cutting edge 14. One end of the cutting edge 14 is connected to the sharp tip 15, while the other end is continuous with the extension line of the crest 5 at the cutting portion 1. The portion where the grinded surfaces 12 cross each other functions as the cutting edge 14, and the portion continuous with the crest 5 does not have a function of cutting the living tissue.

Accordingly, the sharp tip 15 is positioned at approximately a center of the pressed surface 11 in the width direction. As a result, the suture needle can pass through the living tissue with a good balance about the sharp tip 15, when the suture needle cuts the living tissue.

As described above, the cutting edges 13 from the sharp tip 15 are formed to extend toward the body portion 2 than the cutting edge 14 from the sharp tip 15. Therefore, the portion where the cutting edge 14 is formed can cut the living tissue with three cutting edges 13 and 14. At the portion towards the body portion 2 from the portion from the cutting edge 14 to the crest 5, the living tissue can be cut by the two cutting edges 13, and the cut region can be expanded by the crest 5.

As described above, in the suture needle A according to the present embodiment, both end portions of the pressed surface 11 in the width direction are removed by the grinded surfaces 12, but the surface thereof is not ground. Therefore, at the cutting edges 13 formed by the intersection of the pressed surface 11 and the grinded surfaces 12, the portion inward from the surface of the pressed surface 11, which is produced by the cold wiredrawing process and has the highest hardness, is exposed. Accordingly, the cutting edge having high hardness can be realized.

As described above, in the suture needle A according to the present embodiment, the cutting edge having high hardness can be realized by utilizing all effects, which are the work hardening produced by performing a cold wiredrawing process to an austenitic stainless steel, to which a hardening by a hardening process cannot be expected, to elongate a structure thereof in a fiber, a work hardening produced by forming the pressed surface 11 at the portion corresponding to the cutting portion 1, and the effect in which the pressed surface 11 is formed as the surface constituting the cutting portion 1 without performing the grinding process, and the portion having the highest hardness of the material is exposed at the cutting edges 13 formed by the intersection of the pressed surface 11 and the grinded surfaces 12.

Figure 4A:
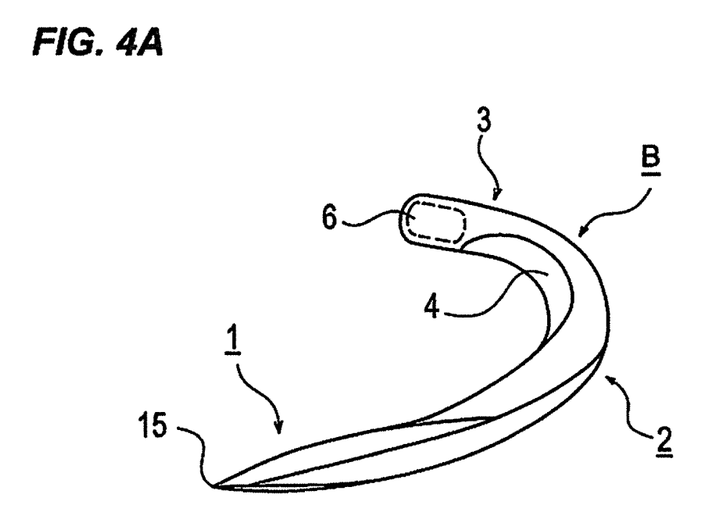
FIG. 4A is a view illustrating an overall structure of a suture needle according to the embodiment of the present invention.
Figure 4B:
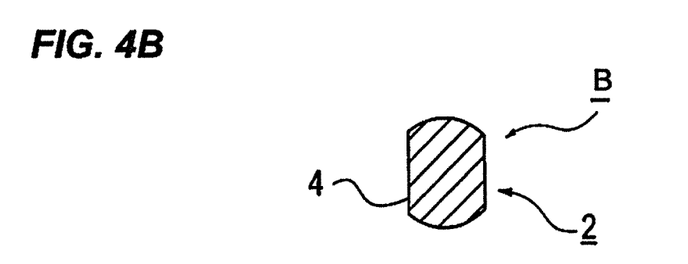
FIG. 4B is a further view illustrating an overall structure of a suture needle according to the embodiment of the present invention.
Figure 5A:
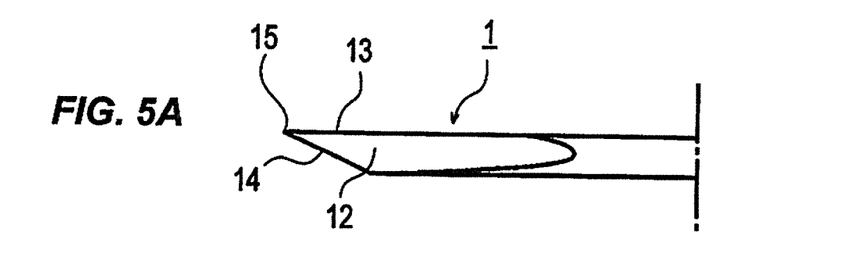
FIG. 5A is a view illustrating a structure of a leading end portion of the suture needle including a cutting portion.
Figure 5B:
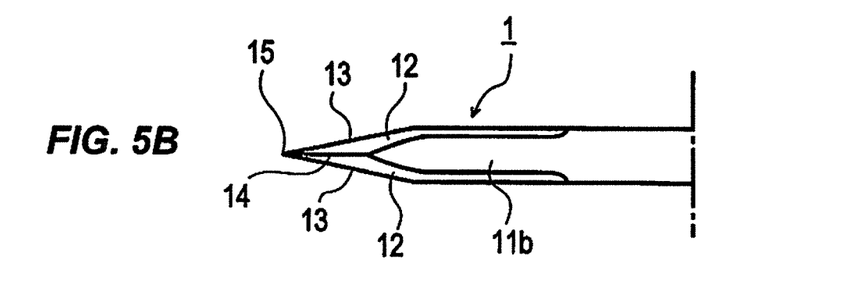
FIG. 5B is a further view illustrating a structure of a leading end portion of the suture needle including a cutting portion.
Figure 5C:
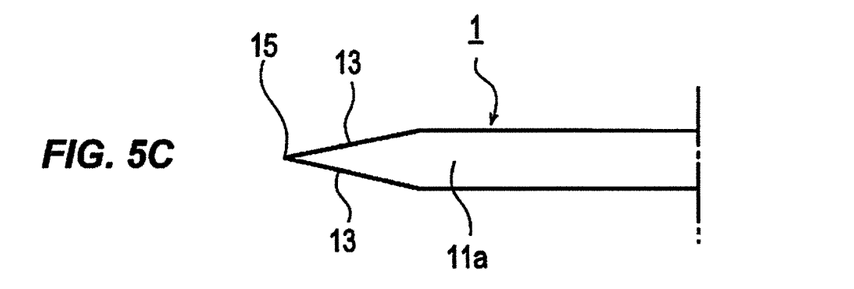
FIG. 5C is a further view illustrating a structure of a leading end portion of the suture needle including a cutting portion.

In the present embodiment, the cross-section of the cutting portion is triangle, so that one surface is formed as the pressed surface 11. However, in a suture needle B in which a Cutting portion is press-formed into an elliptic shape (see FIG. 4(b) like a P needle illustrated in FIGS. 4 and 5, the upper and lower surfaces are formed as the pressed surfaces 11a and 11b. In this case, the intersections of one of the pressed surfaces 11 and the two grinded surfaces 12 are formed as the cutting edges 13. The cross-section of the cutting portion described above is included in the present invention.

A burr is inevitably deposited on the cutting edges 13 formed by the intersection of the pressed surface 11 or 11a and the grinded surfaces 12 and on the cutting edge 14 formed by the intersection of two grinded surfaces 12 due to the grinding of these cutting edges 13 and 14. The burr gives damage to the living tissue, when the suture needle passes through the living tissue, so that the burr has to be removed. Therefore, at least the cutting portion 1 is subject to a chemical polishing or electrolytic polishing, or a polishing with the use of a buff, a grinding stone having an extremely fine abrasive grain, or a plastic wrap.

A base material of the pressed surface 11 is slightly removed by the polishing described above. However, in the suture needle A according to the present invention, the removal of the base material of the pressed surface 11 caused by the polishing described above is different from the removal of the base material by the grinding, and the obtained surface is defined as the pressed surface 11.

Next, a comparison in hardness between the suture needle A according to the present embodiment and a conventional R needle (suture needle so illustrated in FIG. 4) will be described. Plural suture needles A according to the present embodiment were manufactured, and Vickers hardness on the pressed surface 11 of the cutting portion 1 was measured. Vickers hardness of the cutting portion 1 of each of plural R needles, which were the conventional products, was measured. As a result, the highest measured value at the cutting portion 1 of the needle A according to the present embodiment was 624 of Vickers hardness (the same is applied below), the lowest measured value was 551, and the average value was 593.8. In the conventional R needle, the highest measured value was 486 of Vickers hardness, the lowest measured value was 453, and the average value was 474.5.

The difference in the average value between the suture needle A according to the present embodiment and the conventional R needle was 119.3 as described above, which indicates that the suture needle A according to the present embodiment realizes sufficiently high hardness compared to the conventional R needle.

A sharpness test (measurement of piercing resistance) for the suture needle A according to the present embodiment and the R needle was carried out. In this test, a Porvair (registered trademark), which was a synthetic resin sheet having a thickness of 1.10 mm, was used as a material to be pierced, wherein force (Newton, N) upon piercing the material to be pierced was measured.

Ten samples of the suture needle A were used, and each of the samples pierced the material to be pierced ten times. As a result, the average value of the first pierces of 10 samples was 0.804 N, the average value of the second pierces was 0.866 N, the average value of the third pierces was 0.920 N, the average value of the fourth pierces was 0.960 N, the average value of the fifth pierces was 1.020 N, the average value of the sixth pierces was 1.067 N, the average value of the seventh pierces was 1.110 N, the average value of the eighth pierces was 1.122 N, the average value of the ninth pierces was 1.168 N, and the average value of the tenth pierces was 1.188 N.

Five samples of the R needle were used, and each of the samples pierced the material to be pierced ten times. As a result, the average value of the first pierces of 5 samples was 1.249 N, the average value of the second pierces was 1.470 N, the average value of the third pierces was 1.619 N, the average value of the fourth pierces was 1.731 N, the average value of the fifth pierces was 1.827 N, the average value of the sixth pierces was 1.878 NI the average value of the seventh pierces was 2.013 N, the average value of the eighth pierces was 2.109 N, the average value of the ninth pierces was 2.149 N, and the average value of the tenth pierces was 2.212 N.

When the average values of the piercing resistances were simply averaged for comparison, the average value for the suture needle A was 1.022 N, while the average value for the R needle was 1.826 N. Therefore, the suture needle A can reduce the piercing resistance by 0.804 N, compared to the conventional R needle. The measurement and test described above were carried out for the suture needle A. However, in the suture needle B, the enhancement in the hardness of the cutting portion and the reduction in the piercing resistance can similarly be realized.

INDUSTRIAL APPLICABILITY

In the medical suture needle according to the present invention, the cutting portion is made of at least one pressed surface 11. Therefore, the cutting edge 13 having high hardness can be formed, thus advantageous.

The cutting edges formed by the intersection of the pressed surface and the two grinded surfaces are longer than the cutting edge formed by the intersection of the two grinded surfaces. Therefore, the cross-sectional area of the cutting portion is increased, whereby an excellent effect of being capable of increasing the bending strength can be obtained.

The time required for the grinding process can be shortened, compared to the conventional suture needle. Therefore, the effect of being capable of simplifying the production process can be obtained.

DESCRIPTION OF REFERENCE NUMERALS

A, B medical suture needle
1 cutting portion
2 body portion
3 proximal end part
4 plane
5 crest
6 blind hole
11 pressed surface
12 grinded surface
13, 14 cutting edge
15 tip

The invention claimed is:

1. A method of producing a medical suture needle, comprising the steps of:
   forming a first pressed surface by press working to a material of the medical suture needle;
   forming a first ground surface by grinding the material such that a first cutting edge is formed at an intersection of the first pressed surface and the first ground surface;
   forming a second ground surface by grinding the material such that a second cutting edge is formed at an intersection of the first pressed surface and the second ground surface and a third cutting edge is formed at an intersection of the first ground surface and the second ground surface,
   wherein the first cutting edge, the second cutting edge and the third cutting edge are formed such that a leading end where one end of the first cutting edge, one end of the second cutting edge and one end of the third cutting edge are concentrated is positioned at the center of the pressed surface in a width direction of the first pressed surface.

2. The method of producing a medical suture needle according to claim 1, wherein the first cutting edge, the second cutting edge and the third cutting edge are formed such that the first cutting edge and the length of the second cutting edge are longer than the third cutting edge.

3. The method of producing a medical suture needle according to claim 2, wherein a crest is formed on the surface of the material opposite to the first pressed surface during the press working.

4. The method of producing a medical suture needle according to claim 3, wherein the third cutting edge is formed such that another end of the third cutting edge is continuous with the crest.

5. The method of producing a medical suture needle according to claim 2, wherein a second pressed surface is formed on the surface of the material opposite to the first pressed surface during the press working.

* * * * *